United States Patent [19]

Sellstedt et al.

[11] 4,137,325

[45] Jan. 30, 1979

[54] ANTISECRETORY OXAMIC ACID ESTERS

[75] Inventors: John H. Sellstedt, Pottstown; Charles J. Guinosso; David A. Shriver, both of King of Prussia; Dieter H. Klaubert, West Chester, all of Pa.

[73] Assignee: American Home Products Corporation, New York, N.Y.

[21] Appl. No.: 778,516

[22] Filed: Mar. 17, 1977

[51] Int. Cl.² .................. A61K 31/22; A61K 31/535; A61K 31/44; A61K 31/40

[52] U.S. Cl. .............................. 424/311; 424/248.53; 424/263; 424/267; 424/274; 424/285; 424/304

[58] Field of Search ................................ 424/311, 300

[56] References Cited

PUBLICATIONS

*Journal American Chemical Society*, vol. 74, 4011–4012 — Richardson et al.

*Primary Examiner*—Frederick E. Waddell
*Attorney, Agent, or Firm*—Richard K. Jackson

[57] ABSTRACT

Variously substituted oxanilic acid esters possessing anti-secretary activity are useful anti-ulcer agents.

15 Claims, No Drawings

ANTISECRETORY OXAMIC ACID ESTERS

DESCRIPTION OF THE INVENTION

In accordance with this invention there is provided a process for treating peptic ulcer disease which comprises administering to an animal suffering from peptic ulcers an N-substituted lower alkyl or phenyl ester of oxamic acid.

The anti-ulcer agents of this invention function in their anti-secretory capacity to reduce (1) total gastric volume, (2) hydrogen ion secretion, or (3) hydrogen ion concentration. The reduction of any one of these parameters aids in attenuating the general debilitating influence of a peptic ulcer.

The anti-secretory agents useful in the process of this invention are the following N-substituted lower alkyl or phenyl oxamic acid esters in which the N-substituent is:
phenyl;
2-carbamyl-3-methoxyphenyl—;
2-carbamyl-3-hydroxyphenyl—;
2-carbamyl-3-benzyloxyphenyl—;
2-carbamyl-3-dimethylaminophenyl—;
2-carbamyl-3-ethyloxalamidophenyl—;
2-carbamyl-3,5-dimethoxyphenyl—;
2-carbamyl-4,6-dimethylphenyl—;
2-carbamyl-4,6-dichlorophenyl—;
2-cyano-3-dimethylaminophenyl—;
2-cyano-3-piperidinophenyl—;
4-methoxyphenyl—;
4-methoxy-2-nitrophenyl—;
4-nitrophenyl—;
3-fluorophenyl—;
benzyl—;
biphenylyl—;
phenyl,methyl—;
4-phenoxyphenyl—;
3-methylphenyl—;
4-pyridyl—;
3-pyridyl—;
2-nitro-4-trifluoromethylphenyl—;
1-naphthyl—;
4-oxo-4H-1-benzopyran-2-yl—;
4-chlorophenyl—;
2-cyano-3-aminophenyl—;
2-cyano-4-nitrophenyl—;
2-cyano-3-diethylaminophenyl—;
2-carbamyl-3-ethylmethylaminophenyl—;
2-cyano-3-pentoxyphenyl—;
2-cyano-3-(1-pyrrolidinyl)phenyl—;
2-carbamyl-3-(1-pyrolidinyl)phenyl—; or
2-cyano-3-(4-morpholinyl)-5-trifluoromethylphenyl.

The preferred compounds for use in this invention are oxanilic acid esters and substituted oxanilic acid esters in which the substituents are as follows:
2-carbamyl-3-methoxy—;
2-carbamyl-3-hydroxy—;
2-carbamyl-3-benzyloxy—;
2-carbamyl-3-dimethylamino—;
2-carbamyl-3-ethyloxalamido—;
2-carbamyl-3,5-dimethoxy—;
2-carbamyl-4,6-dimethyl—;
2-carbamyl-4,6-dichloro—;
2-cyano-3-diemthylamino—;
4-methoxy—;
4-methoxy-2-nitro—;
4-nitro—;
3-fluoro—;
4-phenyl—;
4-phenoxy—;
3-methyl—;
2-nitro-4-trifluoromethyl—;
[1,4-b]butadienylene—;
4-chloro—;
2-cyano-3-amino—;
2-cyano-5-nitro—;
2-cyano-3-diethylamino—;
2-carbamyl-3-ethylmethylamino—; or
2-cyano-3-pentoxy—.

The expression "lower alkyl" employed throughout this application is intended to embrace those alkyl groups having from 1 to 6 carbon atoms and preferably from 1 to 4 carbon atoms.

Each of the compounds disclosed was found active in the following scientifically recognized, standard test for anti-secretory activity:

Male Charles River rats weighing 190–260 grams are deprived of food but not water for 18 hours prior to use. Water is, however, withheld during the experiment. The rats are weighed, anesthetized with ether and the pylorus ligated according to the method of Shay et al., Gastroenterology 26: 906–913 (1954). Treatment or vehicle control is then administered interduodenally (i.d.). Rats are housed two per cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or blood are eliminated. An aliquot of each is frozen for later analysis of pepsin. The pH is measured and 1 ml. of gastric juice is titrated with 0.1N NaOH to a pH of 7.0–7.4. The data are analyzed by an analysis of variance and using the pooled error variance to make t-comparisons between groups.

The use of compounds exhibiting anti-secretory activity in the curative and/or prophylactic treatment of peptic ulcer disease is an established, beneficial procedure.

The potency of each compound is reported at the end of the example illustrating its production. The potency reported is the lowest dose administered at which two of the three parameters (a) total gastric volume, (b) hydrogen ion secretion, and (c) hydrogen ion concentration, were significantly decreased.

EXAMPLE 1

[2-(aminocarbonyl)-3-methoxyphenylamino]oxoacetic acid ethyl ester

6-Amino-o-anisamide(8.75 g.) is condensed with 6.2 ml. of ethyl oxalyl chloride in 100 ml. methylene chloride in the presence of 9.6 ml. of pyridine at 10° C. Aqueous work-up and evaporation of the methylene chloride followed by recrystallization from ethanol gives the title compound, m.p. 170°–173° C.

Anal. Calcd. for $C_{12}H_{14}N_2O_5$: C, 54.13; H, 5.30; N, 10.52. Found: C, 54.36; H, 5.20; N, 10.66. Potency: 12.5 mg/kg.

EXAMPLE 2

[2-(Aminocarbonyl)-3-(dimethylamino)-phenylamino]oxoacetic acid ethyl ester

Following the procedure of Example 1, 2-amino-6-dimethylaminobenzamide and ethyl oxalyl chloride are condensed to yield the title compound, m.p. 133°–135° C.

Elemental Analysis: $C_{13}H_{17}N_3O_4$ Calcd: C, 55.90; H, 6.14; N, 15.05. Found: C, 56.04; H, 6.21; N, 14.54. Potency: 5 mg/kg.

2-Amino-6-dimethylaminobenzamide is prepared by adding a suspension of 2-dimethylamino-6-nitrobenzonitrile and hydrazine hydrate in ethanol to a suspension of Raney nickel in ethanol while maintaining the reaction temperature at about 65° C. The mixture is then heated to reflux for about half an hour, filtered through Celite and evaporated to dryness. The solid product may be recrystallized from ethanol or used neat in the reaction with ethyl oxalyl chloride.

2-Dimethylamino-6-nitrobenzonitrile is prepared from molar equivalents of 2,6-dinitrobenzonitrile and dimethylamine hydrochloride in dimethylformamide in the presence of aqueous KOH.

EXAMPLE 3

[2-(Aminocarbonyl)-3-(benzyloxy)phenylamino]oxoacetic acid ethyl ester

2-Amino-6-benzyloxybenzamide is treated with ethyl oxalyl chloride as in Example 1 to give the ester, m.p. 151°–153° C.

Anal. Calcd. for $C_{18}H_{18}N_2O_5$: C, 63.15; H, 5.30; N, 8.18. Found: C, 63.31; H, 5.47; N, 8.36. Potency: 10 mg/kg.

2-Amino-6-benzyloxybenzamide is prepared by the Raney nickel reduction of 2-benzyloxy-6-nitrobenzonitrile (E. Cortes & F. Walls, Boll Inst. Quim. Univ. Nach. Auton. Mex. 16, 71 (1964); C.A. 63, 533c (1965) as in Example 2, m.p. 158°–160° C.

Anal. Calcd. for $C_{14}H_{14}N_2O_2$: C, 69.40; H, 5.83; N, 11.56. Found: C, 69.25; H, 6.10; N, 11.69.

EXAMPLE 4

[2-(Aminocarbonyl)-3-(hydroxy)phenylamino]oxoacetic acid ethyl ester

A mixture of 3.4 g. of [2-(aminocarbonyl)-3-benzyloxyphenylamino]oxoacetic acid ethyl ester and 0.3 g. of 5% Pd on charcoal is hydrogenated until hydrogen uptake ceases. The mixture is filtered through celite; the filtrate is evaporated and the residue is recrystallized to give pure product, m.p. 200°–202° C.

Anal. Calcd. for $C_{11}H_{12}N_2O_5$: C, 52.38; H, 4.80; N, 11.11. Found: C, 51.87; H, 4.80; N, 10.94. Potency: 10 mg/kg.

EXAMPLE 5

2,2'-[2-(Aminocarbonyl)-1,3-phenylenediimino]bis[2-oxoacetic acid]diethyl ester 2,6-Diaminobenzamide is oxalated in the usual manner using two times the usual amounts of pyridine and ethyl oxalyl chloride. Recrystallization from acetonitrile gives the title compound, m.p. 220°–222° C.

Anal. Calcd. for $C_{15}H_{17}N_3O_7$: C, 51.28; H, 4.88; N, 11.96. Found: C, 50.97; H, 4.84; N, 11.90. Potency: 10 mg./kg.

EXAMPLE 6

[2-(Aminocarbonyl)-4,6-(dimethyl)phenylamino]oxoacetic acid ethyl ester

2-Amino-3,5-dimethylbenzamide is treated with ethyl oxalyl chloride and pyridine as in Example 1 to give the desired product, m.p. 177°–179° C.

Anal. Calcd. for $C_{13}H_{16}N_2O_4$: C, 59.08; H, 6.10; N, 10.60. Found: C, 59.03; H, 6.20; N, 10.72. Potency: 2.5 mg./kg.

2-Amino-3,5-dimethylbenzamide. Liquid phosgene (55 g.) is added to a stirred solution of 30.1 g. (0.182 mol.) of 2-amino-3,5-dimethylbenzoic acid in 300 ml. of dioxane. The temperature is raised to 40°–45° C. and held for 2 hr. The mixture is stirred overnight at room temperature and filtered. The filter cake is washed with diethyl ether, giving 33 g. (95%) of 6,8-dimethyl-2H-3,1-benzoxazine-2,4(1H)-dione; m.p.>300° C. The isatoic anhydride is then added to 435 ml. of 1 M. $NH_4OH$. The mixture is stirred overnight at room temperature, brought to reflux for 2 hr. cooled, filtered, and crystallized (EtOH), giving 13.4 g. (47%) of product, m.p. 162°–167° C.

Anal. Calcd. for $C_9H_{12}N_2O$: C, 65.83; H, 7.37; N, 17.06. Found: C, 65.71; H, 7.42; N, 16.89.

EXAMPLE 7

[2-(Aminocarbonyl)-3,5-(dimethoxy)phenylamino]oxoacetic acid ethyl ester

Treatment of 2-amino-4,6-dimethoxybenzamide with ethyl oxalyl chloride and pyridine as in Example 1 gives the title compound, m.p. 198°–208° C.

Anal. Calcd. for $C_{13}H_{16}N_2O_6$: C, 52.70; H, 5.44; N, 9.46. Found: C, 52.75; H, 5.56; N, 9.54. Potency: 10 mg./kg.

2-Amino-4,6-dimethoxybenzamide is prepared from 2-amino-4,6-dimethoxybenzoic acid as in Example 6, m.p. 117°–119° C.

Anal. Calcd. for $C_9H_{12}N_2O_3$: C, 55.09; H, 6.17; N, 14.28. Found: C, 55.01; H, 6.21; N, 14.12.

2-Amino-4,6-dimethoxybenzoic acid is known [H. Newman and R. Angier, J. Org. Chem., 34, 3484 (1969)].

EXAMPLE 8

[2-(Aminocarbonyl)-4,6-(dichloro)phenylamino]oxoacetic acid ethyl ester

2-Amino-3,5-dichlorobenzamide is oxalated as in Example 1, m.p. 168°–170° C.

Anal. Calcd. for $C_{11}H_{10}Cl_2N_2O_4$: C, 41.00; H, 2.95; N, 13.66; Cl, 23.23. Found: C, 43.32; H, 3.20; N, 9.23; Cl, 23.48. Potency: 10 mg./kg.

2-Amino-3,5-dichlorobenzamide is prepared from the corresponding anthranilic acid as in Example 6, m.p. 176°–181° C.

Anal. Calcd. for $C_7H_6N_2OCl_2$: C, 41.00; H, 2.96; N, 13.66; Cl, 34.58. Found: C, 40.69; H, 2.81; N, 13.24; Cl, 33.24.

EXAMPLE 9

[2-Cyano-3-dimethylaminophenylamino]oxoacetic acid ethyl ester

To a solution of 3.4 g. of crude 2-amino-6-dimethylaminobenzonitrile and 1.6 g. of pyridine in 50 ml. of methylene chloride at 0° C. is added dropwise 2.7 g. of ethyl oxaly chloride in 25 ml. of methylene chloride.

The solution is stirred at 0° C. for 3 hr., warmed to room temperature and water is added. The organic phase is separated, dried and evaporated to give a yellow solid which is recrystallized from benzenehexane to yield 3.2 g. of pure product, m.p. 124°–126° C.

Anal. Calcd. for $C_{13}H_{15}N_3O_3$: C, 59.76; H, 5.74; N, 16.08. Found: C, 59.47; H, 5.74; N, 16.08 Potency: 20 mg./kg.

The crude benzonitrile is prepared in the following way:

To a suspension of 5.7 g. of 2-dimethylamino-6-nitrobenzonitrile in 20 ml. of methanol and 17 ml. of conc. hydrochloric acid is added 5.3 g. of iron powder in portions. The mixture is stirred for ½ hr., diluted with 200 ml. of water and extracted with methylene chloride which is dried and evaporated in vacuo to yield crude benzonitrile.

EXAMPLE 10

[2-Cyano-3-(1-piperidinyl)phenylamino]oxoacetic acid ethyl ester

This is prepared from 2-amino-6-(1-piperidinyl)-benzonitrile in a manner analogous to the preparation given in Example 1, m.p. 98°–100° C.

Anal. Calcd. for $C_{16}H_{19}N_3O_3$: C, 63.77; H, 6.36; N, 13.94. Found: C, 63.76; H, 6.37; N, 13.76. Potency: 20 mg./kg.

2-Amino-6-(1-piperidinyl)benzonitrile is prepared from 2-nitro-6-(1-piperidinyl)benzonitrile as in Example 9 by iron reduction.

2-Nitro-6-(1-piperidinyl)benzonitrile is prepared as follows:

To a solution of 19.3 g. of 2,6-dinitrobenzonitrile in 300 ml. of DMF is added 25.5 g. of piperidine and the resulting solution is warmed to 85° C. and kept at that temperature until the reaction is complete. The reaction mixture is poured into water, the product is filtered and dried, m.p. 119°–121° C.

Anal. Calcd. for $C_{12}H_{13}N_3O_2$: C, 62.32; H, 5.67; N, 18.17. Found: C, 62.32; H, 5.82; N, 18.26.

EXAMPLE 11

4'-Methoxyoxanilic acid ethyl ester

The title compound is known in the literature: A. Puitti et al., Ber. Deut. Chem., 31, 330–336(1898). It is crystallized from ethanol, m.p. 100°–104° C.

Potency: 10 mg./kg.

EXAMPLE 12

4'-Methoxy-2'-nitrooxanilic acid ethyl ester

The title compound is known in the literature: Zh. Obshch. Khim., 7, 2471–7 (1937). It is crystallized from ethanol, m.p. 154°–160° C.

Potency: 25 mg./kg.

EXAMPLE 13

4'-Nitrooxanilic acid ethyl ester

The title compound is known in the literature: G. Tierie, Rec. Trav. Chim., 52, 420–4 (1933). It is crystallized from acetic acid, m.p. 169°–172° C.

Potency: 25 mg./kg.

EXAMPLE 14

3'-Fluorooxanilic acid ethyl ester m-Fluoroaniline (5.55 g, 0.05 mole) is condensed with 6.16 ml. (0.055 mole) of ethyl oxalyl chloride in 100 ml. of dichloromethane in the presence of 7.9 g. (0.1 mole) pyridine at 10° C. with stirring, giving 9.26 g. of the title compound, m.p. 85°–89° C. after crystallization from ethanol.

Anal. Calcd. for $C_{10}H_{10}FNO_3$: C, 57.0; H, 4.78; N, 6.64. Found: C, 56.45; H, 4.87; N, 6.61. Potency: 25 mg./kg.

EXAMPLE 15

Benzyloxamic acid ethyl ester

The title compound is known in the literature: T. Curtius and K. Raschig, J. Prakt. Chem., 125, 446 (1930). It is crystallized from di-ethyl ether-pentane, m.p. 47°–50° C.

Potency: 10 mg./kg.

EXAMPLE 16

4'-Phenyloxanilic acid ethyl ester

The title compound is known in the literature: A. G. Richardson et al., J. Am. Chem. Soc., 74, 4011 (1952). It is crystallized from ethanol, m.p. 128°–132° C.

Potency: 25 mg./kg.

EXAMPLE 17

N-Methyloxanilic acid ethyl ester

The title compound is known in the literature: P. A. Petyunin et al., Zh. Obshch. Khim., 27, 1554 (1957). It is distilled at 108° C. (0.25 mm).

Potency: 10 mg./kg.

EXAMPLE 18

4'-Phenoxyoxanilic acid ethyl ester

The title compound is known in the literature: P. A. Petyunin et al., Khim.-Farm. Zh. 1(12), 7 (1967). It is crystallized from ethanol, m.p. 97°–100° C.

Potency: 10 mg./kg.

EXAMPLE 19

3'Methyloxanilic acid ethyl ester

The title compound is known in the literature: P. A. Petyunin et al., Zh. Obshch. Khim., 24, 1078 (1954). It is crystallized from benzene-hexane, m.p. 56°–60° C.

Potency: 10 mg./kg.

EXAMPLE 20

(4-Pyridyl)oxamic acid ethyl ester

4-Aminopyridine (2.82 g., 0.03 mole) is condensed with 3.7 ml. (0.033 mole) of ethyl oxalyl chloride in a manner similar to example 14, giving 1.26 g. of the title compound, m.p. 110°–113° C., after crystallization from diethyl ether.

Anal. Calcd. for $C_9H_{10}N_2O_3$: C, 55.66; H, 5.19; N, 14.43. Found: C, 55.88; H, 5.15; N, 14.64. Potency: 10 mg./kg.

EXAMPLE 21

(3-Pyridyl)oxamic acid ethyl ester

3-Aminopyridine (2.82 g., 0.03 mole) is condensed with 3.7 ml. (0.033 mole) of ethyl oxalyl chloride in a manner similar to example 14, giving 2.36 g. of the title compound, m.p. 98°–100° C., after crystallization from diethyl ether.

Anal. Calcd. for $C_9H_{10}N_2O_3$: C, 55.66; H, 5.19; N, 14.43. Found: C, 55.40; H, 5.13; N, 14.71. Potency: 10 mg./kg.

EXAMPLE 22

Oxanilic acid phenyl ester

The title compound is known in the literature: R. Stolli et al., Chem. Ber., 54, 1213 (1921). It is crystallized from ethanol, m.p. 136°–139° C.

Potency: 10 mg./kg.

EXAMPLE 23

2'-Nitro-4'-(trifluoromethyl)oxanilic acid ethyl ester

4-Amino-3-nitrobenzotrifluoride (3.21 g., 0.03 mole) is condensed with 3.7 ml. (0.033 mole) of ethyl oxalyl chloride in a manner similar to example 14, giving 7.01 g. of the title compound, m.p. 124°–126° C., after crystallization from ethanol.

Anal. Calcd. for $C_{11}H_9F_3N_2O_5$: C, 43.1; H, 2.96; N, 9.16. Found: C, 42.97; H, 3.02; N, 9.28. Potency: 10 mg./kg.

EXAMPLE 24

(1-Naphthyl)oxamic acid ethyl ester

The title compound is known in the literature: P. P. T. Sah et al., J. Chin. Chem. Soc. (Peking), 14, 101 (1946); Chem. Abstr., 43, 6973g (1949). It is crystallized from diethyl ether, m.p. 105°–107° C.

Potency: 12.5 mg./kg.

EXAMPLE 25

(4-Oxo-4$\underline{H}$-1-benzopyran-3-yl)oxamic acid ethyl ester

To a suspension of 1.61 grams (0.01 mole) of 2-amino-4$\underline{H}$-1-benzopyran-4-one[prepared by the method of Kawase et al., Bull. Chem. Soc. Japan, 35, 1869 (1962)] in 30 ml. of methylene chloride, is added 0.8 g. (0.01 mole) of pyridine followed by the dropwise addition of 1.37 g. (0.01 mole) of ethyl oxalyl chloride in 20 ml. of methylene chloride. The resulting solution is stirred for one hour, poured into distilled water and the organic layer separated, dried and evaporated to yield the title compound. Recrystallization from ethyl acetate gives 2.2 g. (80% yield) of the title compound, m.p. 167°–169° C.

Anal. Calcd. for $C_{13}H_{11}NO_5$: C, 59.76; H, 4.25; N, 5.36. Found: C, 59.40; H, 4.09; N, 5.44. Potency: 25 mg./kg.

EXAMPLE 26

(4-Chlorophenyl)oxamic acid ethyl ester

The title compound is known in the literature: Farmaco, Ed. Sci., 22(9), 717–34 (1967). It is crystallized from ethanol, m.p. 149°–152° C.

EXAMPLE 27

(3-amino-2-cyanophenylamino)oxoacetic acid ethyl ester

A mixture of 11.5 g. of (3-nitro-2-cyanophenylamino) oxoacetic acid ethyl ester, 4.4 g. of 10% Pd/C and 18 g. of cyclohexene in 220 ml. of ethanol is refluxed for 35 minutes, filtered through celite and evaporated to dryness. The residue is chromatographed on silicon gel with chloroform and the title compound is recrystallized from ethanol, m.p. 133°–136° C.

Anal. Calcd. for $C_{11}H_{11}N_3O_3$: C, 56.64; H, 4.76; N, 18.02. Found: C, 56.58; H, 4.64; N, 18.20. Potency: 10 mg./kg.

(3-nitro-2-cyanophenylamino)oxoacetic acid ethyl ester is prepared by oxalation of 2-amino-6-nitrobenzonitrile as in example 1, m.p. 111°–113° C.

Anal. Calcd. for $C_{11}H_9N_3O_5$: C, 50.19; H, 3.45; N, 15.97. Found: C, 50.11; H, 3.44; N, 15.99.

2-amino-6-nitrobenzonitrile is obtained by iron reduction of 2,6-dinitrobenzonitrile in a manner similar to example 9, m.p. 195°–197° C.

Anal. Calcd. for $C_7H_5N_3O_2$: C, 51.54; H, 3.09; N, 25.76. Found: C, 50.94; H, 2.98; N, 25.66.

EXAMPLE 28

(3-cyano-5-nitrophenylamino)oxoacetic acid ethyl ester 3-amino-5-nitrobenzonitrile is oxalated as in example 1 to give the title compound, m.p. 114°–116° C.

Anal. Calcd. for $C_{11}H_9N_3O_5$: C, 50.19; H, 3.45; N, 15.97. Found: C, 50.29; H, 3.42; N, 16.06. Potency: 25 mg./kg.

3-amino-5-nitrobenzonitrile is prepared by iron reduction of 3,5-dinitrobenzonitrile as in example 9, m.p. 168°–170° C.

Anal. Calcd. for $C_7H_5N_3O_2$: C, 51.53; H, 3.09; N, 25.76. Found: C, 51.30; H, 3.03; N, 25.84.

EXAMPLE 29

[2-cyano-3-(diethylamino)phenylamino]oxoacetic acid ethyl ester

Treatment of 2-amino-6-diethylamino-benzonitrile with ethyl oxalyl chloride as in example 1 yields the title compound, m.p. 57°–59° C.

Anal. Calcd. for $C_{15}H_{19}N_3O_3$: C, 62.27; H, 6.62; N, 14.52. Found: C, 62.23; H, 6.43; N, 14.62. Potency: 1 mg./kg.

2-amino-6-diethylaminobenzonitrile is prepared by cyclohexene — Pd/C reduction of the corresponding nitro compound similar to example 27. The crude amine is uded directly.

2-diethylamino-6-nitrobenzonitrile is prepared as follows:

To an equimolar mixture of ethyl iodide and 2-ethylamino-6-nitrobenzonitrile in DMF is added an equimolar amount of sodium hydride (50% in oil). After 1 hr., the reaction is poured into water and extracted with methylene chloride. The dried extracts are passed through silicon gel to give the desired product which is recrystallized from hexane, m.p. 39°–41° C.

Anal. Calcd. for $C_{11}H_{13}N_3O_2$: C, 60.26; H, 5.98; N, 19.19. Found: C, 59.82; H, 5.97; N, 18.88.

2-ethylamino-6-nitrobenzonitrile is prepared from 2,6-dinitrobenzonitrile and ethylamine as in example 10.

EXAMPLE 30

[2-(aminocarbonyl)-3-(ethylmethylamino)-phenylamino]oxoacetic acid ethyl ester 2-amino-6-ethyl methylaminobenzamide is treated with ethyl oxalyl chloride as in example 1, m.p. 85°–88° C.

Anal. Calcd. for $C_{14}H_{19}N_3O_4$: C, 57.32; H, 6.53; N, 14.33. Found: C, 57.20; H, 6.55; N, 14.22. Potency: 25 mg./kg.

2-amino-6-ethylmethylaminobenzamide is prepared by Raney nickel reduction of 2-ethylmethylamino-6-nitrobenzonitrile as in example 2.

The benzonitrile is prepared from 2,6-dinitrobenzonitrile and ethylmethylamino as in example 10, m.p. 60°–63° C.

EXAMPLE 31

[(2-cyano-3-pentyloxyphenyl)amino]oxoacetic acid ethyl ester 2-amino-6-pentyloxybenzonitrile is oxalated as in example 1, m.p. 78°–81° C.

Anal. Calcd. for $C_{16}H_{20}N_2O_4$: C, 63.14; H, 6.62; N, 9.21. Found: C, 62.99; H, 6.67; N, 9.18. Potency: 5 mg./kg.

2-amino-6-pentyloxybenzonitrile is prepared by Pd/C, cyclohexene reduction of 2-nitro-6-pentyloxybenzonitrile as in example 27, m.p. 70°–73° C.

Anal. Calcd. for $C_{12}H_{16}N_2O$: C, 70.56; H, 7.90; N, 13.72. Found: C, 70.40; H, 7.70; N, 13.63.

2-nitro-6-pentyloxybenzonitrile is known: A. Russell and L. M. Addison, J. Am. Chem. Soc. 65, 2379 (1943)

EXAMPLE 32

[2-cyano-3-(1-pyrrolidinyl)phenylamino]oxoacetic acid ethyl ester

Prepared as in example 1, m.p. 138°–141° C.

Anal. Calcd. for $C_{15}H_{17}N_3O_3$: C, 62.70; H, 5.96; N, 14.63. Found: C, 62.81; H, 5.98; N, 14.61 Potency: 20 mg./kg.

2-amino-6-pyrrolidinylbenzonitrile is prepared by iron reduction as in example 9, m.p. 112°–114° C.

Anal. Calcd. for $C_{11}H_{13}N_3$: C, 70.56; H, 7.00; N, 22.44 Found: C, 70.51; H, 6.71; N, 22.50

2-nitro-6-pyrrolidinylbenzonitrile is prepared from pyrrolidine and 2,6-dinitrobenzonitrile as in example 10, m.p. 110°–112° C.

Anal. Calcd. for $C_{11}H_{11}N_3O_2$: C, 60.82; H, 5.10; N, 19.35. Found: C, 61.04; H, 5.14; N, 19.59.

EXAMPLE 33

[2-(aminocarbonyl)-3-(1-pyrrolidinyl)phenylamino]oxoacetic acid ethyl ester 2-amino-6-pyrrolidinylbenzamide and ethyl oxalyl chloride as in example 1 gives the title compound, m.p. 149°–153° C.

Anal. Calcd. for $C_{15}H_{19}N_3O_4$: C, 59.00; H, 6.27; N, 13.76. Found: C, 58.97; H, 6.20; N, 13.72. Potency: 10 mg./kg.

2-amino-6-pyrrolidinylbenzamide is prepared by Raney nickel reduction of 2-nitro-6-pyrrolidinylbenzonitrile as in example 2, m.p. 144°–146° C.

Anal. Calcd. for $C_{11}H_{15}N_3O_4$: C, 64.36; H, 7.37; N, 20.47. Found: C, 64.55; H, 7.35; N, 20.62.

EXAMPLE 34

[2-cyano-3-(4-morpholinyl)-5-(trifluoromethyl)-phenylamino]oxoacetic acid ethyl ester 2-amino-4-trifluoromethyl-6-morpholinylbenzonitrile is oxalated in the usual manner, m.p. 106°–109° C.

Anal. Calcd. for $C_{16}H_{16}N_3O_4F_3$: C, 51.76; H, 4.34; N, 11.32. Found: C, 52.07; H, 4.40; N, 11.33. Potency: 25 mg/kg.

2-amino-4-trifluoromethyl-6-morpholinylbenzonitrile is prepared by cyclohexene — Pd/C reduction as in example 27, m.p. 166°–171° C.

Anal. Calcd. for $C_{12}H_{12}N_3OF_3$: C, 53.14; H, 4.46; N, 15.49. Found: C, 53.01; H, 4.43; N, 15.38.

2-nitro-4-trifluoromethyl-6-morpholinylbenzonitrile is prepared from 2,6-dinitro-4-trifluoromethylbenzonitrile and morpholine as in example 10, m.p. 174°–178° C. 2,6-dinitro-4-trifluoromethylbenzonitrile is known: J. R. Beck, J. Org. Chem. 37, 3224 (1972).

The anti-secretory agents of this invention may be administered orally or parenterally. Liquid compositions include sterile solutions for parenteral administration as well as suspensions, emulsions, syrups and elixirs of the active ingredients for oral administration. The compounds may be employed alone as the sole basis for treatment or they may be advantageously employed in conjunction with a treatment regimen utilizing a conventional antacid such as calcium carbonate, magnesium carbonate, bismuth carbonate, aluminum or magnesium hydrated oxides, magnesium glycinate, magnesium trisilicate, calcium trisilicate, or sodium bicarbonate to maintain gastric acidity from about a pH of 3 to 5 or higher. Likewise, the anti-secretory agents of this invention may be used in conjunction with anti-cholinergic agents or $H_2$-receptor blocking agents.

Pharmaceutical compositions containing the anti-secretory agents of this invention are formulated conventionally with a solid or liquid carrier. Solid carriers acceptable for use in the administration of anti-secretory agents via tablets, capsules or powders, include magnesium carbonate, magnesium stearate, talc, sugar, lactose, pectin, dextrin, starch, gelatin, tragacanth, methyl cellulose, sodium carboxymethyl cellulose, low melting waxes and cocoa butter. Additional optional ingredients include flavoring agents, lubricants, solubilizers, suspending agents, binders and disintegrants. The quantity of active anti-secretory agent in a solid or liquid compsoition may be varied widely, such as from about 10 to 80 percent or more.

Unit dosage forms containing from about 10 to 500 milligrams of the substituted oxamic acid esters are especially suitable for use in oral administration.

What is claimed is:

1. A process for treating peptic ulcer disease which comprises administering, orally or parenterally, to a mammal in need thereof an anti-secretory amount of an N-substituted lower alkyl or phenyl ester of oxamic acid in which the N-substituent is:

phenyl;
   2-carbamyl-3-methoxyphenyl—;
   2-carbamyl-3-hydroxyphenyl—;
   2-carbamyl-3-benzyloxyphenyl—;
   2-carbamyl-3-dimethylaminophenyl—;
   2-carbamyl-3-ethyloxalamidophenyl—;
   2-carbamyl-3,5-dimethoxyphenyl—;
   2-carbamyl-4,6-dimethylphenyl—;
   2-carbamyl-4,6-dichlorophenyl—;
   4-methoxyphenyl—;
   4-methoxy-2-nitrophenyl—;
   4-nitrophenyl—;
   3-fluorophenyl—;
   benzyl—;
   biphenylyl—;
   phenyl, methyl—;
   4-phenoxyphenyl—;
   3-methylphenyl—;
   2-nitro-4-trifluoromethylphenyl—;
   1-naphthyl—;
   4-chlorophenyl—; or
   2-carbamyl-3-ethylmethylaminophenyl—.

2. A process of claim 1 in which said oxanilic acid ester is ethyl 2-carbamyl-3-methoxy oxanilate.

3. A process of claim 1 in which said oxanilic acid ester is ethyl-3-benzyloxy-2-carbamyloxanilate.

4. A process of claim 1 in which said oxanilic acid ester is ethyl 2-carbamyl-3-hydroxyoxanilate.

5. A process of claim 1 in which said oxanilic acid ester is ethyl 2-carbamyl-3-dimethylamino-oxanilate.

6. A process of claim 1 in which said oxanilic acid ester is 2-carbamyl-3-ethyloxalamido-oxanilate.

7. A process of claim 1 in which said oxanilic acid ester is ethyl 2-carbamyl-3,5-dimethoxyoxanilate.

8. A process of claim 1 in which said oxanilic acid ester is ethyl 2-carbamyl-4,6-dimethyloxanilate.

9. A process of claim 1 in which said oxanilic acid ester is ethyl 2-carbamyl-4,6-dichlorooxanilate.

10. A process of claim 1 in which said oxanilic acid ester is ethyl 4-methoxy oxanilate.

11. A process of claim 1 in which said oxanilic acid ester is ethyl N-methyloxanilate.

12. A process of claim 1 in which said oxanilic acid ester is ethyl 4-phenoxyoxanilate.

13. A process of claim 1 in which said oxanilic acid ester is ethyl 3-methyloxanilate.

14. A process of claim 1 in which said oxanilic acid ester is phenyl oxanilate.

15. A process of claim 1 in which said oxanilic acid ester is ethyl 4-chlorooxanilate.

* * * * *